United States Patent
Riemenschneider

(10) Patent No.: US 10,322,220 B2
(45) Date of Patent: Jun. 18, 2019

(54) METHOD AND DEVICE FOR EXTRACORPOREAL BLOOD TREATMENT

(71) Applicant: B. BRAUN AVITUM AG, Melsungen (DE)

(72) Inventor: Heiko Riemenschneider, Wagenfurth (DE)

(73) Assignee: B. Braun Avitum AG (DE)

(*) Notice: Subject to any disclaimer, the term of this patent is extended or adjusted under 35 U.S.C. 154(b) by 85 days.

(21) Appl. No.: 15/482,084

(22) Filed: Apr. 7, 2017

(65) Prior Publication Data
US 2017/0296726 A1   Oct. 19, 2017

(30) Foreign Application Priority Data
Apr. 15, 2016 (DE) .................. 10 2016 107 024

(51) Int. Cl.
A61M 1/16 (2006.01)
A61M 1/34 (2006.01)

(52) U.S. Cl.
CPC ........ *A61M 1/1605* (2014.02); *A61M 1/1656* (2013.01); *A61M 1/341* (2014.02);
(Continued)

(58) Field of Classification Search
None
See application file for complete search history.

(56) References Cited

U.S. PATENT DOCUMENTS 4,906,375 A * 3/1990 Heilmann ............ B22D 2/006
 210/500.23
6,806,947 B1 * 10/2004 Ekdahl ................ A61M 1/3626
 356/339

(Continued)

FOREIGN PATENT DOCUMENTS

DE 102010052070 A1 5/2012
DE 102011103261 A1 11/2012
(Continued)

OTHER PUBLICATIONS

Krick et al—On-Line Hemodiafiltration: The Journey and the Vision, Karger, 2011, pp. 131-135 (Year: 2011).*
(Continued)

*Primary Examiner* — Krishnan S Menon
*Assistant Examiner* — Bradley R Spies
(74) *Attorney, Agent, or Firm* — RatnerPrestia

(57) ABSTRACT

A method for extracorporeal blood treatment using a medical device including at least a dialyzer device, with the following steps: start of blood treatment by means of hemodialysis on the basis of default values for the hemodialysis; determination of current values or ratios of at least one blood flow, an ultrafiltration quantity, a substitution quantity or a type of substitution; recording of a therapy progress on the basis of an output signal of a sensor means; determination of a time of formation of a secondary membrane on the dialyzer by determination of a cross rate in the dialyzer device; change from the hemodialysis to a hemodiafiltration with post-dilution after a predetermined period of time has elapsed; and regulation of the substitution quantity during hemodiafiltration with post-dilution. Corresponding tools for carrying out the method are arranged in a device for extracorporeal blood treatment.

10 Claims, 3 Drawing Sheets

(52) U.S. Cl.
CPC ........ *A61M 1/3406* (2014.02); *A61M 1/3413* (2013.01); *A61M 1/3437* (2014.02); *A61M 1/3441* (2013.01); *A61M 2205/3317* (2013.01); *A61M 2205/3334* (2013.01); *A61M 2205/50* (2013.01); *A61M 2205/502* (2013.01); *A61M 2205/707* (2013.01)

(56) References Cited

U.S. PATENT DOCUMENTS

| | | |
|---|---|---|
| 2005/0203493 A1 | 9/2005 | Kuroda et al. |
| 2012/0298581 A1 | 11/2012 | Wehmeyer et al. |
| 2013/0303961 A1 | 11/2013 | Wolff et al. |
| 2017/0182238 A1 | 6/2017 | Mochizuki |

FOREIGN PATENT DOCUMENTS

| | | |
|---|---|---|
| EP | 1655043 A2 | 7/2000 |
| EP | 1867353 A1 | 12/2007 |
| EP | 2714128 B1 | 8/2016 |
| EP | 3195890 A1 | 7/2017 |
| WO | 2015022537 A1 | 2/2015 |
| WO | 2016043186 A1 | 3/2016 |

OTHER PUBLICATIONS

German Search Report for German Application No. 10 2016 107 024.6, dated Nov. 16, 2016, including English translation, 17 pages.
European Search Report with English language translation for Application No. 17 165 291.0, dated Aug. 18, 2017, 14 pages.

\* cited by examiner

METHOD AND DEVICE FOR EXTRACORPOREAL BLOOD TREATMENT

CROSS REFERENCE TO RELATED APPLICATIONS

This application claims priority to German application DE 10 2016 107 024.6 filed Apr. 15, 2016, the contents of such application being incorporated by reference herein.

FIELD OF THE INVENTION

The invention relates to a method and a device for extracorporeal blood treatment, and relates in particular to a method and device for extracorporeal blood treatment with delayed hemodiafiltration start of treatment in connection with a regulation to maximum cross rate within the scope of a hemodiafiltration treatment, preferably an online hemodiafiltration treatment.

BACKGROUND OF THE INVENTION

A known device for extracorporeal blood treatment comprises at least a treatment unit such as, for example, a dialyzer and/or a dialyzer device, or a filter, ultrafilter or plasma filter of a different filter unit with a semipermeable membrane which separates the treatment unit into two chambers. An extracorporeal blood circulation permits a flow of blood taken from a patient through the first chamber and back to the patient. At the same time, a dialysis fluid (treatment fluid) flows in the opposite direction through an appropriately designed circulation via the second chamber.

The known device comprises moreover an infusion line for a substitution fluid, a fluid inlet line connected with the second chamber on the inlet side, and a fluid outlet line connected with the second chamber on the outlet side. Moreover, sensors are provided for determining a first parameter relating to the blood volume of a patient, a second parameter relating to a ultrafiltration flow rate or a weight loss rate of the patient, a third parameter relating to a conductivity or concentration of a fluid flowing through the fluid line and/or the infusion line, and a fourth parameter relating to a infusion flow rate. A control unit carries out a control procedure for compensating a fluctuation of the blood volume and an adjusting sequence for applying a transmembrane pressure with values for maximising the convective exchange processes.

In the known device the transmembrane pressure and the blood flow are correlated, and depending on the speed of the blood flow and its changes different functions are carried out, for example, a new operating mode is started or an operating mode is stopped.

In renal replacement therapies with devices of the known type various complications can occur. For example, devices are designed to be able to intervene, if a calculable (excessive) worsening of the therapy result could occur in the case of a parameter intervention by the user which had not been optimally adjusted.

For example, when starting the therapy, i.e. at a time when already all therapy parameters and the form of therapy have been selected, one can try to achieve as fast as possible also a predetermined blood flow in order to start therapy. If this is not immediately successful, and therapy starts with a lower blood flow, a hemoconcentration of the blood in the dialyzer may occur. This is presently systematically monitored but treatment as such is permitted by indicating, for example, an exceeding of the ultrafiltration/cross rate wherein due to existing limit values (30% at a therapeutically aimed at maximum value of 25%) only a small margin exists. Another case occurs in therapy, if due to a problematic access the blood flow needs to be reduced even if only temporarily. The user is not allowed to reduce and/or change the prescribed substitution quantity or type of therapy (for example from post-dilution to pre-dilution) without consultation with the physician.

Moreover, presently known assemblies do not take into account the forming of a secondary membrane during the first minutes. Complications in a renal replacement therapy also result in a clotting in the extracorporeal circulation, for example, due to a too low heparin dosing, a too low flow and too high filtration rates which regularly manifests itself by an increase of the filter inlet pressure. By this, proteins can deposit on the filter inside and result in a decrease of the filtration performance. Due to the deposit, the secondary membrane is formed, which would have to be tackled by the user by a sufficient heparinization, a pre-dilution or the increase of the substitute, and by decrease of the filtration (decline of the screening coefficient) in the case of formation of secondary membranes a reduction of the filtration pressure Pf and thus an increase of the transmembrane pressure TMP results.

Since the precise mechanisms of occurrence of the secondary membranes are not yet fully known, and moreover measures influencing them are possible only in a limited way in hemofiltration due to the risk of hemolysis, here as well a consultation with the physician in each case is required, or, as mentioned above, the secondary membrane formation is adversely unconsidered in known assemblies. Nor are any processes carried out automatically which evaluate the cross-flow rate and/or cross rate and prevent an application error. Hence, the user must immediately interpret correctly all consequences from a warning message of the device or system but nevertheless can decide only for two sub-optimal approaches. On the one hand, he or she can interrupt therapy until the blood flow is adequate again. But the end of treatment is also delayed automatically as a result. On the other hand, he or she can accept the membrane load and the associated reduction in effectiveness and subsequently a reduced therapy result.

SUMMARY OF THE INVENTION

It is therefore an objective of the invention to provide a method and device for extracorporeal blood treatment which overcome the above mentioned disadvantages and problems, and automatically support a user and react correctly in critical situations.

Moreover, for example, application errors resulting from temporary problems of access shall be recognizable and it shall be possible to compensate them until an adequate and sufficient blood flow is achieved.

This objective is achieved according to aspects of the invention by a device for extracorporeal blood treatment with the features of the first independent claim, and by a corresponding method with the features the second independent claim. Advantageous further embodiments of the invention are the subject matter of the dependent claims.

The invention relates to the general idea to provide within the scope mentioned above a mere constant size regulation of the substitution flow in view of a maximum performance of a dialyzer associated with an automatically delayed start of a hemodiafiltration in preferably the type of treatment of hemodiafiltration and/or HDF (post-dilution) and/or "post HDF" or HDF (post) whereby stress is reduced and a therapeutic goal can be achieved more easily. In other words, by a special regulation a delayed online HDF therapy start after sufficient formation of the secondary membrane and by an automated guarantee of a maximum possible dialyzer performance throughout the therapeutic process a maximum possible therapy result shall be guaranteed. For this purpose, the constant size regulation of the substitution flow is carried out, which saves precalculations for the physician, and provides assurance to a user, for example, a nurse, that the treatment occurs continuously in a maximum possible physiological range. The formation of the secondary membrane and the start of the HDF (with post-dilution) with the correct (substitution) quantity occurs automatically and safely and consistent with the respective application.

Regulation and/or control implements a simple and safe method in order to give the user in critical situations the time required in each case until, for example, an attending physician or senior personnel can carry out necessary therapy changes. The method and the device prevent application errors and minimize the risk of a dialyzer blocking in the post HDF therapy due to excessive cross rates. It is no longer required to pay attention to a sufficient formation of the secondary membrane but the user can already in advance and/or during preparation select all corresponding parameters of the therapy since a time of switching from HD to online HDF and a substitution quantity are automatically calculated and switched on.

Thus, a system performing the method and comprising the device supports the user and monitors the process sequence by providing security. Infused quantities are continuously displayed as well as values to be expected which are possible and/or achievable with a present setting. A patient related value of a proportional quantity can be individually adjusted at any time so that the user can advantageously turn again to other important treatment parameters. The physician determines a maximum cross rate in a patient-related manner. The system then controls all necessary parameters independently. In other words, instead of a target quantity (substitution) only a patient-related maximum ratio of the substitution in a fixed ratio to the blood flow is used. Thus, without any risk, the possible maximum of therapy effectiveness is achieved and precalculations for technical reasons made by the physician until now are omitted.

In detail, the above advantages are realized, and the objective is achieved by a device for extracorporeal blood treatment comprising a dialyzer device and designed for the performance of a hemodialysis and a hemodiafiltration with post-dilution, the device for extracorporeal blood treatment further comprising: a user interface to be operated and/or read by a user for starting the blood treatment with hemodialysis on the basis of default values for the hemodialysis; at least one recording and/or computing unit for determining current values and/or ratios of at least one blood flow, an ultrafiltration quantity, a substitution quantity and/or a type of substitution; a sensor means for recording a therapy progress on the basis of an output signal of a sensor means; a determination means for determining an ultrafiltration rate in the dialyzer device; a determination means for determining a time of formation of a secondary membrane in the dialyzer device on the basis of the determined ultrafiltration rate; a switching means for changing from hemodialysis to a hemodiafiltration with post-dilution after a predetermined period of time has elapsed; and a regulating means for regulating the substitution quantity during hemodiafiltration with post-dilution.

Moreover, the objective is achieved by a method for extracorporeal blood treatment by using a medical device for extracorporeal blood treatment, which comprises at least one dialyzer device, with the following steps: start of blood treatment with hemodialysis on the basis of default values for the hemodialysis; determination of current values and/or ratios of at least one blood flow, an ultrafiltration quantity, a substitution quantity and/or a type of substitution; recording of a therapy progress on the basis of an output signal of a sensor means; determination of an ultrafiltration rate in the dialyzer device; determination of a time of formation of a secondary membrane in the dialyzer device on the basis of the determined ultrafiltration rate; change from the hemodialysis to a hemodiafiltration with post-dilution after a predetermined period of time has elapsed; and regulation of the substitution quantity during hemodiafiltration with post-dilution.

Preferably, the predetermined period of time is a period of time after a first recording of a blood flow on the sensor means. Change from hemodialysis to hemodiafiltration with post-dilution occurs automatically, if at the predetermined time a predetermined cross rate is determined, wherein at the predetermined cross rate a predetermined treatment blood flow is assumed as having been achieved and the secondary membrane is assumed as comprising a predetermined state of formation.

Preferably, the predetermined period of time is initially approximately 3 to 5 minutes and the device and/or the method is designed, after start of treatment, to adjust an actual period of time on the basis of default values and currently calculated values, and to start hemodiafiltration with post-dilution in an automatically delayed manner.

Preferably, the first recording of the blood flow occurs with a blood sensor arranged on the air detector means as the sensor means and the assumed state of formation of the secondary membrane is derived from the calculated cross rate.

Preferably, the substitution quantity is regulated by the regulating means in accordance with a default of an application wherein the substitution quantity does not exceed a predetermined maximum percentage portion of the blood flow.

Preferably, the substitution quantity is regulated by the regulating means to a constant value or quantity.

Preferably, the predetermined maximum percentage portion is 25 to 30% of the blood flow.

Preferably, the substitution quantity is reduced automatically by, the regulating means, when the blood flow falls below a predetermined minimum quantity, and a message informing on the reduced substitution quantity is issued for a user.

Preferably, the substitution quantity is automatically limited by the regulating means when a predetermined cross rate is achieved and a message informing on the limitation of the substitution quantity is issued for the user.

Preferably, all necessary parameters can be predetermined by the user and the device and/or the method is designed for reducing maximum quantities automatically, if this is necessary.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
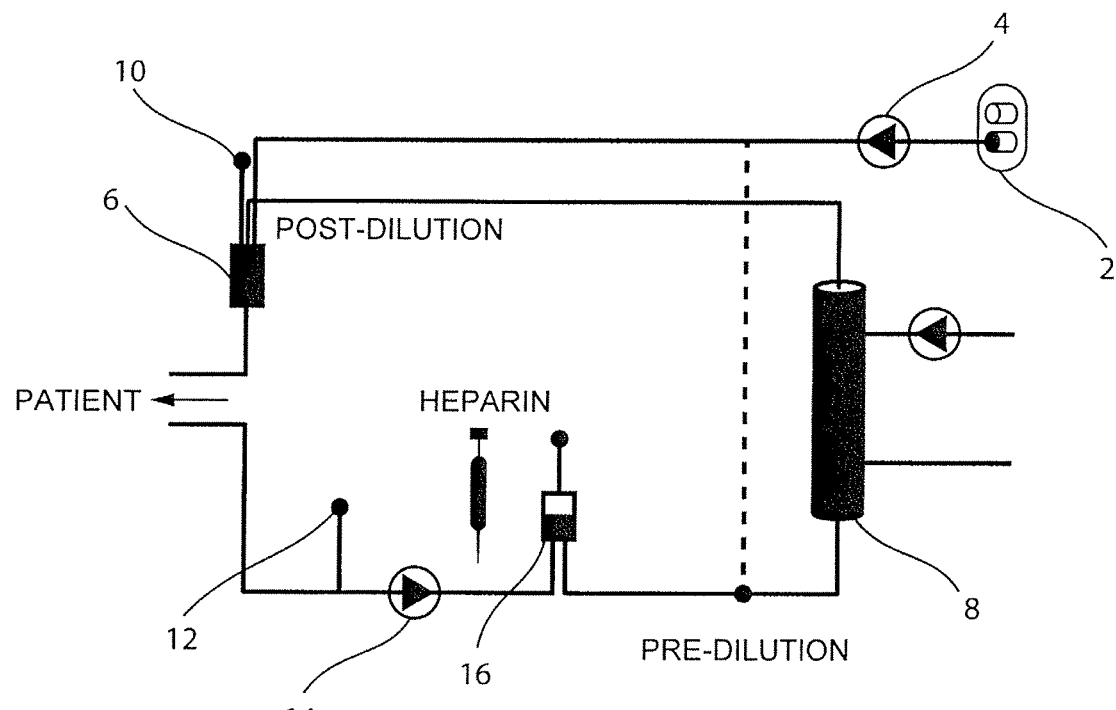
FIG. 1 is a schematic view of a blood circulation with post-dilution and/or pre-dilution during online hemodiafiltration (online HDF) arranged in an embodiment of the method and the device for extracorporeal blood treatment.

In the following description of the figures the same elements and/or components or elements and/or components having the same effect can be designated in the same way or with the same reference numerals and can be expediently described non-redundantly. Where a subsequent embodiment corresponds functionally at least to a previous embodiment, i.e. corresponding functions, assemblies and/or process sequences or operating procedures are equally covered, expediently only differences are treated.

FIG. 1 shows a schematic view of a blood circulation with post-dilution and/or pre-dilution during online hemodiafiltration (online HDF) used and/or arranged in an embodiment of the method and the device for extracorporeal blood treatment.

A device for extracorporeal blood treatment such as, for example, a dialyzer machine for cleaning the blood of a patient, if, for example, his or her renal function is impaired or ceased, comprises a dialyzer, through which on the one hand the patient's blood to be cleaned flows and through which on the other hand dialysis fluid or dialysis solution flows, preferably according to the countercurrent principle, wherein certain dissolved substances (for example, urea) from the blood pass into the dialysis fluid.

Moreover, the device for extracorporeal blood treatment has an arterial blood circulation in which a blood pump is arranged, a venous blood circulation, a dialysis fluid supply line supplying fresh dialysis fluid to the dialyzer, a dialysis fluid discharge line, which discharges and/or purges used dialysis fluid from the dialyzer, a substitution line and a substitution pump which supplies substituate (electrolyte solution) flowing in the substitution line to a dilution point located upstream (pre-dilution) or downstream (post-dilution) of the dialyzer in the arterial and/or venous blood circulation. Furthermore, a control unit measures the concentration of blood, for example, in a predetermined dilution channel section, and controls the substituate quantity supplied by the substitution pump for preventing excessive blood thickening and for continuous compensation of ultrafiltration exceeding the necessary elimination of liquid and thus avoiding volume losses, on the basis of the measured or an evaluated blood concentration. A device for extracorporeal blood treatment of the above mentioned type can be designed for preparing, supplying and substituting substituate according to the principle of online hemodiafiltration (online HDF) or online hemofiltration. In the case of an online HDF method, the substitution fluid and/or the substituate is extracted from the dialysis fluid and infused either upstream or downstream of the filter.

System, structure, components and functioning of the above mentioned device for extracorporeal blood treatment are in itself fundamentally known, and are therefore included herein and not described further.

The blood circulation with post-dilution and/or pre-dilution shown in FIG. 1 is part of an device for extracorporeal blood treatment as described above. From an online, i.e. substituate originating during a current therapy from a substituate source 2 in or on the device for extracorporeal blood treatment is transported from an online substituate pump 4 through a dilution line to an air detector means 6. A venous blood line coming from a dialyzer 8, a high flux dialyzer in the present embodiment, opens out into the air detector means 6. Moreover, a venous pressure transducer 10 is connected with the air detector means 6. An arterial blood line coming from a patient opens out into the dialyzer 8, in the course of which blood line are arranged an arterial pressure transducer 12, an arterial blood pump 14, another pressure transducer 16 on an arterial expansion chamber upstream of the dialyzer 8 and a point of introduction for a pre-dilution. Moreover, arterially also a heparin addition (anticoagulant) controlled by the device for preventing blood coagulation can be provided.

Figure 2:
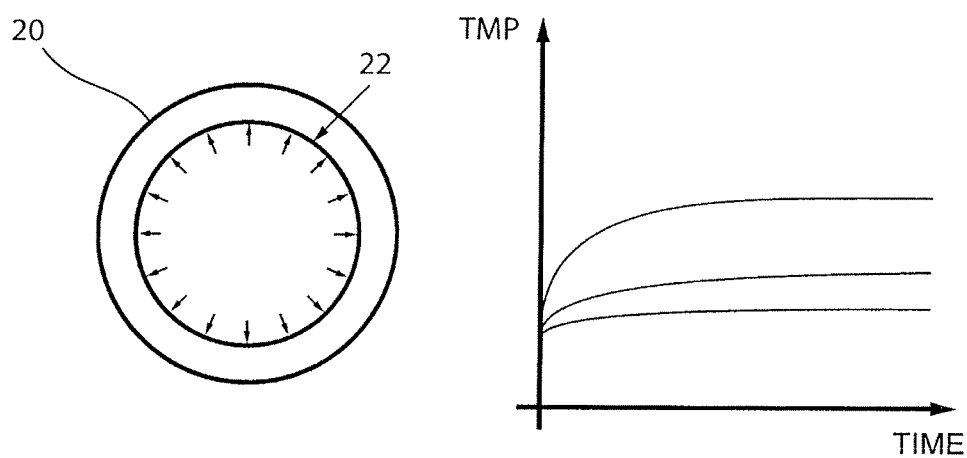
FIG. 2 is a schematic view for explanation of the formation of a secondary membrane in a dialyzer device.

FIG. 2 shows a schematic view for explanation of the formation of a secondary membrane in a dialyzer device. A secondary membrane occurs as a diffusion layer 22 on the hollow membranes 20 in the dialyzer 8 during a current blood treatment by attaching, for example, cellular blood components and proteins and/or plasma proteins to the dialyzer membrane. Formation of a secondary membrane is coupled with the transmembrane pressure TMP. The transmembrane pressure TMP in the dialyzer 8 is a hydrostatic pressure gradient between the blood side and dialysis fluid side which is used by the ultrafiltration.

Function and integrity of the dialyzer 8 can be monitored on the machine side by measurement of the dynamic inlet and outlet pressures. For example, by assuming a linear pressure drop a mean pressure for the blood side and a mean pressure for the dialysis fluid side can be determined from the inlet and outlet pressures the difference of which results in a mean transmembrane pressure TMP. Said mean transmembrane pressure TMP can then be used for monitoring as to whether the filter is blocked by deposits and formation of a secondary membrane.

As is shown on the right side of FIG. 2, the transmembrane pressure TMP rises at first at the beginning of an HDF dialysis and during formation of a secondary membrane and then reaches at least approximately a plateau.

Although the transmembrane pressure TMP rising at the beginning is accompanied by a blocking or clogging of the pores of the dialyzer, for example, by accumulating proteins and this virtually corresponds to a decrease of the filter surface, whereby the efficiency of the entire therapy may be decreased, also advantages result due to the formation of the secondary membrane and/or diffusion layer, such as, for example, a suppression of complement activation, a decrease of thrombogenicity, a suppression of thrombocyte activation and a decrease of protein absorption.

In the present embodiment it is assumed that a sufficient secondary membrane has formed after approximately 3 to 5 minutes after start of therapy at low blood flow and minimum ultrafiltration.

In an example, a hematocrit level of approx. 35% at the dialyzer inlet and a hematocrit level of approx. 50% at the dialyzer outlet can occur at the beginning of the HDF dialysis at a dialysis fluid flow of approx. 30% of the blood flow and post-dilution. Due to formation of the secondary membrane and/or along with the increase of the transmembrane pressure TMP, these amounts can change, for example, when assuming a decrease of the blood volume by 15% to approx. 41% on the dialyzer inlet and approx. 59% on the dialyzer outlet. The hematocrit increase is inversely proportional to the change of blood volume, i.e. the decrease of the relative blood volume is characterized by the increase of the hematocrit level. By measuring the hematocrit level a relative change of the (relative) blood volume can be detected.

Figure 3:
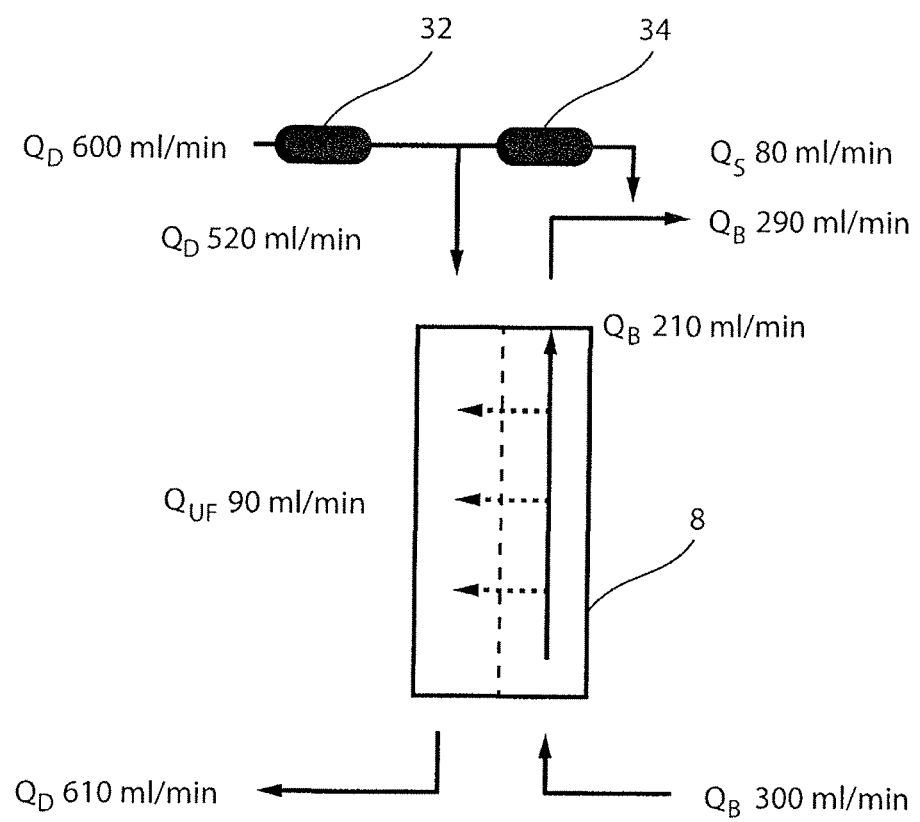
FIG. 3 is a schematic view for illustration of flow ratios during online HDF inside a dialyzer.

FIG. 3 shows a schematic view for illustration of flow ratios during online HDF inside a dialyzer, for example, of the dialyzer 8 according to FIG. 1. Moreover, in FIG. 3 with a DF filter 32 and/or dialysis fluid filter as a first filter stage and with a HDF filter 34 as a second filter stage in the dialysis fluid flow are designated which are likewise arranged in the device for extracorporeal blood treatment. Moreover, $Q_D$ designates a dialysis fluid flow, $Q_B$ designates a blood flow, $Q_{UF}$ designates an ultrafiltration flow and $Q_S$ designates a substituate flow for the pre-dilution or post-dilution.

As is shown in FIG. 3, the entire original dialysis fluid flow, in the present embodiment for example $Q_D$=600 ml/min, is directed through the DF filter 32. Downstream of the DF filter 32 part of the dialysate flow $Q_D$, for example an amount of 520 ml/min, is directed through the dialyzer 8. The remaining part of the dialysis fluid flow $Q_D$ is in addition directed through the HDF filter 34 and downstream of said filter provided as a substituate flow $Q_S$=80 ml/min for pre-dilution or post-dilution.

Countercurrently to the dialysis fluid flow through the dialyzer 8, the blood flow $Q_B$ flows through the dialyzer which blood flow in the present embodiment is, for example, at the dialyzer inlet $Q_B$=300 ml/min and at the dialyzer outlet still $Q_B$=210 ml/min. From this a cross rate or cross rate of ultrafiltration of $Q_{UF}$=90 ml/min or approx. 27% is calculated in the present embodiment. In other words, $Q_{UF}$=90 ml/min of fluid pass through the membrane of the dialyzer 8 (convective transport). As is indicated on the right side of the HDF filter, the substituate flow $Q_S$=80 ml/min is added post-dilutively to blood flow $Q_B$=210 ml/min on the dialyzer outlet so that a venously flowing off blood flow $Q_B$=290 ml/min results.

Since in the case of post-dilution the ratio of blood to total ultrafiltration should be 25 to 30% maximum, and at the same time the total substitution volume should be approximately one third of the body weight of the patient, in one example the following calculated values result for post-dilution for a patient with a body weight of 81 kgs:

body weight: 81 kgs
weight loss: 3 kgs
treatment time: 5 hours
30% of 81 kgs=27 l substitution volume
27 l substitution volume+3 l weight loss=30 l net ultrafiltration quantity 30 l in 5 hours treatment time yields an ultrafiltration rate of 6 l/h or 100 ml/min. The entire ultrafiltration quantity is thus 3 l, and the blood flow $Q_B$ should be at least approx. 350 ml/min.

In accordance with the above description a delayed hemodiafiltration treatment start in connection with a regulation to maximum cross rate of ultrafiltration within the scope of a hemodiafiltration treatment, preferable an online hemodiafiltration treatment, is carried out in the method and the device for extracorporeal blood treatment of the present embodiment.

For this purpose, prior to treatment and as indicated above by way of an example on the basis of practical scales, at first applicable ratios from blood flow, ultrafiltration quantity, substitution quantity and type of substitution are determined or calculated.

Figure 4:
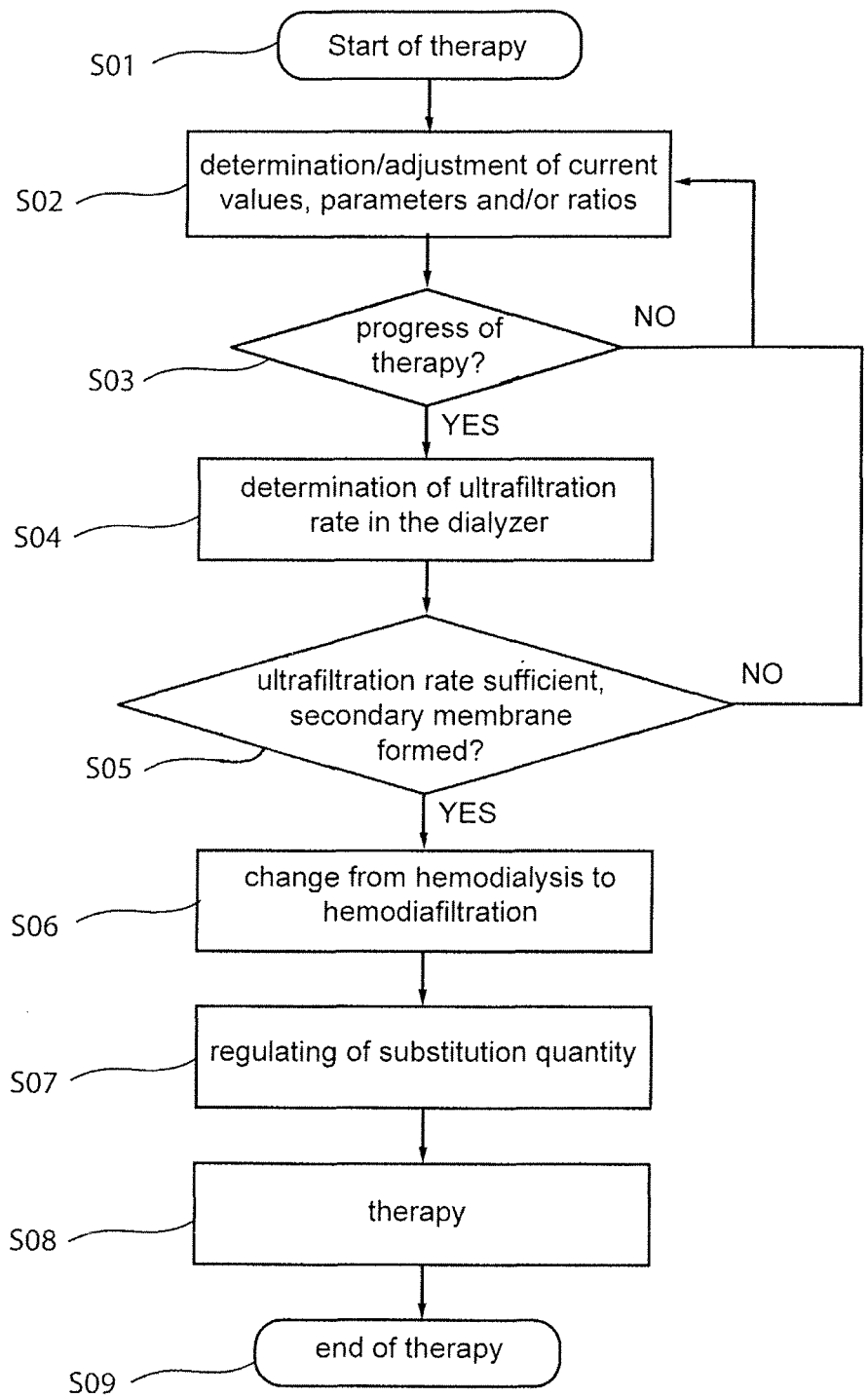
FIG. 4 is a schematically and highly simplified flow chart of the method for extracorporeal blood treatment according to an embodiment

FIG. 4 shows a schematically highly simplified flow chart of the method. After determination of the necessary treatment or therapy parameters and selection or determination of the form of therapy, in a step S01 therapy is started by a user, for example, a nurse in a dialysis station, by means of hemodialysis on the basis of the default values for the hemodialysis. Subsequently, the procedure advances to a step S02.

In step S02 current values and/or parameters and/or ratios at least of blood flow, ultrafiltration quantity, substitution quantity and/or type of substitution are determined or adjusted. The values determined can be modified via the user interface of the device for extracorporeal blood treatment. The user in this stage tries to achieve the predetermined blood flow as fast as possible in order to be able to start the actual therapy. The user can enter all values and parameters but maximum quantities are reduced by the device in an appropriate manner, if necessary. The procedure advances to a next step S03.

In step S03 therapy progress is recorded on the basis of an output signal of a sensor means. For example, the therapy progress can be recorded by recording arrival of a first blood quantity with a blood sensor in or on the air detector equipment 6. If sufficient therapy progress is recorded (YES in step S03), the procedure advances to a next step S04. If therapy has not yet progressed far enough (NO in step S03), the procedure returns to step S02.

In step S04 the ultrafiltration rate and/or the ultrafiltration cross-flow is determined by the membrane in the dialyzer device 8. In other words, a cross rate calculation is carried out. Then the procedure advances to a step S05.

In step S05 it is checked as to whether a cross rate consistent with the other parameters, i.e. the desired treatment blood flow, is reached, and as to whether the secondary membrane is sufficiently formed. If the treatment blood flow is reached and the secondary membrane is sufficiently formed (YES in step S05), the procedure advances to a step S06. If the treatment blood flow is not yet reached and/or the secondary membrane is not yet sufficiently formed (NO in step S05), the procedure returns to step S02. Alternatively it can be provided that the procedure returns to step S04.

In step S06 a delayed start of hemodiafiltration with post-dilution and/or HDF (post) occurs which is carried out automatically in accordance with specifications and calculation. The automatic start of HDF (post), i.e. the change from the initial hemodialysis to hemodiafiltration is to be expected in practice approx. 5 minutes after the first contact with blood on the air detector equipment 6, if an appropriate cross rate has been achieved, i.e. the treatment blood flow is achieved, and the secondary membrane is sufficiently formed. Then, the procedure advances to a step S07.

In step S07 the substitution quantity, i.e. the quantity of the substituate supplied with post-dilution, is adjusted according to default of the application and to 25% to 30% max. of the blood flow.

For example, the substitution quantity can be regulated to a constant value, which is 25% to 30% max. of the blood flow, if the blood flow remains constant, or regulated to a value, which is constantly 25 to 30% max. of the blood flow, if the blood flow changes. In the case of a changing blood flow which is, where applicable, insufficient then, it is provided that the substitution quantity is likewise reduced accordingly in order to maintain the above mentioned percentage amount. In this case the method and the device are configured to issue, for example, via the user interface of the device or the like an indication for the user that the substitution quantity has been automatically reduced.

Subsequent to step S07, in a step S08 shown in a highly simplified manner, further therapy or blood treatment is carried out, and the method and/or its process(es) end at the end of therapy in a step S09.

As has been described above, according to aspects of the invention the maximum performance of the dialyzer is used and maintained. If, for example, by a possibly sub-optimally adjusted parameter intervention of a user, a calculable (massive) worsening of the therapy result could occur, an intervention by the system can be made. Causes for interventions by the system can be varied and, for example, be due to the complexity and diversity of types of application requiring increasingly expert knowledge, a respective personnel key and qualification of operating personnel, no instant availability of the responsible physician, and be the reasons for a reduced therapy result.

The method according to aspects of the invention and the device according to aspects of the invention support the user in applications which directly impair the performance of the dialyzer. Necessary parameters are corrected automatically in the process. In addition, also a note is issued but at any rate in such a case due to the inventive limitation of the substitution to a maximum factor the performance capability of the dialyzer is not impaired. Due to the limitation to a maximum factor, i.e., the constant value regulation of the substitution flow, the dialyzer is no longer burdened beyond limit.

When the cross rate is reached, the substitution quantity is automatically limited and the user is informed accordingly. For example, a display or message can issued as follows:

"Caution: The infused quantity is reduced, the therapeutic goal may possibly not be reached any more." The substitution target quantity can be modified by the user at any time. Likewise he or she can switch on and switch off warnings with respect to the target.

It should be understood that the invention is not limited to the embodiments described and its modifications but that combinations nevertheless obvious for the person skilled in the art of at least parts of said embodiments, modifications and equivalents may result within the scope of protection defined by the subsequent patent claims.

The invention claimed is:

1. A method for extracorporeal blood treatment using a medical device including a dialyzer, the method comprising the steps of:
    starting blood treatment by means of hemodialysis using default values for the hemodialysis;
    determining at least one of current values or ratios for at least one of blood flow, an ultrafiltration quantity, a substitution quantity and/or a type of substitution;
    recording a therapy progress using an output signal of a sensor;
    determining an ultrafiltration rate in the dialyzer to determine whether the ultrafiltration rate is a pre-determined ultrafiltration rate at a pre-determined period of time;
    determining a time of formation of a secondary membrane in the dialyzer using the determined ultrafiltration rate to determine whether the secondary membrane has reached a pre-determined state of formation;
    upon determining that the ultrafiltration rate is the pre-determined ultrafiltration rate and the secondary membrane has reached the pre-determined state of formation, changing from the hemodialysis to a hemodiafiltration with post-dilution after a predetermined period of time has elapsed; and
    regulating substitution quantity during hemodiafiltration with post-dilution.

2. The method of claim 1, wherein the predetermined period of time is a period of time after a first recording of a blood flow by the sensor, and the change from the hemodialysis to the hemodiafiltration with post-dilution occurs automatically.

3. The method of claim 2, wherein the predetermined period of time is initially approximately 3 to 5 minutes and the method further comprises, after start of treatment, adjusting an actual period of time on the basis of default values and currently calculated values, and starting the hemodiafiltration with post-dilution in an automatically delayed manner.

4. The method of claim 2, wherein the first recording of the blood flow is by a blood sensor arranged on an air detector and the predetermined state of formation of the secondary membrane is derived from the determined ultrafiltration rate.

5. The method of claim 1, wherein the substitution quantity is regulated in accordance with a default of an application wherein the substitution quantity does not exceed a predetermined maximum percentage portion of the blood flow.

6. The method of claim 1, wherein the substitution quantity is regulated to a constant value or quantity.

7. The method of claim 5, wherein the predetermined maximum percentage portion is 25 to 30% of the blood flow.

8. The method of claim 5, wherein the substitution quantity is reduced automatically, if the blood flow falls below a predetermined minimum quantity, and the method further comprises issuing a message to a user informing of the reduced substitution quantity.

9. The method of claim 1, wherein the substitution quantity is limited automatically, if the predetermined ultrafiltration rate is reached, and the method further comprises issuing a message to a user informing on the limitation of the substitution quantity.

10. The method of claim 1, wherein all necessary parameters are predetermined by the user and the medical device is configured to reduce maximum quantities automatically.

* * * * *